United States Patent
Ahmavaara

(10) Patent No.: US 6,807,421 B1
(45) Date of Patent: Oct. 19, 2004

(54) METHOD FOR CONTROLLING CONNECTIONS TO A MOBILE STATION

(75) Inventor: Kalle Ahmavaara, Vantaa (FI)

(73) Assignee: Nokia Networks Oy, Espoo (FI)

( * ) Notice: Subject to any disclaimer, the term of this patent is extended or adjusted under 35 U.S.C. 154(b) by 0 days.

(21) Appl. No.: 09/647,132

(22) PCT Filed: Mar. 31, 1999

(86) PCT No.: PCT/FI99/00268

§ 371 (c)(1),
(2), (4) Date: Nov. 1, 2000

(87) PCT Pub. No.: WO99/51051

PCT Pub. Date: Oct. 7, 1999

(30) Foreign Application Priority Data

Mar. 31, 1998 (FI) .............................................. 980736

(51) Int. Cl.[7] .............................................. H04Q 7/20
(52) U.S. Cl. ...................................... 455/438; 370/331
(58) Field of Search .......................... 455/432.1, 432.2, 455/436, 437, 438; 370/467, 468, 331

(56) References Cited

U.S. PATENT DOCUMENTS

| | | | |
|---|---|---|---|
| 5,504,773 A | | 4/1996 | Padovani et al. ............ 375/200 |
| 5,521,963 A | | 5/1996 | Shrader et al. |
| 5,537,417 A | * | 7/1996 | Sharma et al. .............. 709/228 |
| 5,930,714 A | | 7/1999 | Abu-Amara et al. |
| 5,940,381 A | * | 8/1999 | Freeburg et al. ............ 370/331 |
| 6,125,150 A | * | 9/2000 | Wesel et al. ................ 375/265 |
| 6,125,276 A | * | 9/2000 | Lupien ........................ 455/436 |
| 6,201,970 B1 | * | 3/2001 | Suzuki et al. ............... 455/450 |
| 6,212,390 B1 | * | 4/2001 | Rune ........................ 455/456.6 |
| 6,230,013 B1 | * | 5/2001 | Wallentin et al. ........... 455/436 |
| 6,400,966 B1 | * | 6/2002 | Andersson et al. ......... 455/561 |
| 6,650,899 B1 | * | 11/2003 | Stumpert ..................... 455/436 |

FOREIGN PATENT DOCUMENTS

| | | | |
|---|---|---|---|
| CH | 682 867 A5 | 11/1993 | |
| EP | 0 681 406 A1 | 11/1995 | ............ H04Q/7/24 |
| EP | 0 740 486 A2 | 10/1996 | |
| EP | 0 903 883 A1 | 3/1999 | ............ H04L/1/12 |
| JP | 02-015722 | 1/1990 | ............ H04B/7/26 |
| JP | 03/179849 | 8/1991 | ........... H04L/12/56 |
| JP | 04-23695 | 1/1992 | ............ H04Q/7/04 |
| JP | 08-065236 | 3/1996 | ............ H04B/7/26 |
| JP | 09/172461 | 6/1997 | ........... H04L/12/56 |
| WO | WO 95/08899 | 3/1995 | ............ H04Q/7/22 |
| WO | WO 95/15665 | 6/1995 | |
| WO | WO 96/26620 | 8/1996 | |
| WO | WO 98/18282 | 4/1998 | ............ H04Q/7/38 |

OTHER PUBLICATIONS

Michel Mouly, Marie–Bernadette Pautet, The GSM System for Mobile Communications, Radio Frequency Management, pp. 346–349; 396–399, 1992.

(List continued on next page.)

Primary Examiner—Nick Corsaro
(74) Attorney, Agent, or Firm—Cohen, Pontani, Lieberman & Pavane

(57) ABSTRACT

When a mobile station has moved from a network area controlled by a first radio network controller (RNC) to a network area controlled by a second RNC, the utilisation of transmission links in the radio access network is optimized and the transmission delay between the controlling RNC and the radio interface is minimized by relocating the entities which control the connections of the mobile station from the first RNC to the second RNC. Such controlling entities may be, for example, the macrodiversity combining function, radio resource control block, and associated user plane entities.

25 Claims, 5 Drawing Sheets

OTHER PUBLICATIONS

ETSI: Recommendation GSM 05, 01 vol. 3.3.2, Jan. 1991, Section 5, Physical Layer on thee Radio Path.

ETSI TC–SMG "Universal Mobile Telecommunications System (UMTS); UMTS Terrestrial Radio Access (UTRA); Concept Evaluation (UMTS 30.06 version 3.0.0) TR101146". ETSI TR 101 146 V3.0.0, XX, XX, Dec. 1997, pp. 486–590, XP002153734.

"Digital Cellular Telecommunications System (Phase 2+); Channel coding, (GSM 05.03 version 5.3.1)" ETSI European Telecommunications Standard ETS 300909, Aug. 1997, pp. 1–38, XP002194479.

* cited by examiner

METHOD FOR CONTROLLING CONNECTIONS TO A MOBILE STATION

CROSS-REFERENCES TO RELATED APPLICATIONS

This is a U.S. national stage application under 35 U.S.C. §371 of international stage application No. PCT/FI99/00268, filed on Mar. 31, 1999, which date is thereby the filing date of this application under 35 U.S.C. §363. Priority is claimed under 35 U.S.C. §§119(a) and 35 U.S.C. §365(b) from Finnish Patent Application No. 980736, which was filed Mar. 31, 1998, and from which the priority was properly claimed in international stage application No. PCT/FI99/00268.

TECHNICAL FIELD OF THE INVENTION

The invention is directed to a method for optimisation of transmission links in a cellular telecommunications network.

BACKGROUND OF THE INVENTION

FIG. 1 shows an example of a situation which sometimes occur during a hard handover, i.e. when a mobile station 10 changes the base station or base stations 20 it uses. Such a situation may occur, for example, when a mobile station moves from one cells to another in a cellular telecommunication system. FIG. 1 depicts two situations, situation A, when the mobile station 10 is still in the area of the first cell, and situation B, when the mobile station (MS) has moved to the area of the second cell. FIG. 1 shows also base stations (BS) 20, which are controlled by radio network controllers (RNC) 30, 31. The radio network controllers are connected to a mobile switching center (MSC) 40. In the first situation, the mobile station 10 is in position marked by the letter A, having connections to base stations 20 controlled by the first RNC 30. The radio network controller 30 comprises combining 33 and splitting 34 units. Combining units 33 combine uplink signals belonging to the same bearer coming from different base stations, and splitting units replicate downlink signals to more than one base station. The RNC 30 also comprises a protocol control block 32, which executes the protocols needed for communication with the mobile station 10. The RNC 30 forwards the uplink data to, and receives downlink data from, the MSC 40, which communicates with the rest of the telecommunications network.

When the mobile station moves to the position marked by the letter B, the mobile station 10 establishes radio links to the base stations 20. During the handover signaling, the first RNC 30, i.e RNC1 in FIG. 1, establishes the necessary connections B' via RNC2 to base stations 20 controlled by the RNC2, and releases the former connections A' to the base stations 20 controlled by the RNC1. The controlling RNC, i.e., RNC1 in FIG. 1, is commonly called the controlling RNC. The other RNC, i.e., RNC2 in FIG. 1, is commonly called the drift RNC. Further, in some specifications for the UMTS (Universal Mobile Telecommunication System), the interface between two RNCs is called the Iur interface, and the interface between a MSC and RNC is called the Iu interface. These interface names are used in this specification.

The system of FIG. 1, namely the use of a controlling RNC and a drift RNC, has certain drawbacks which arise from the fact, that in situation B the transmission links are routed via two RNC:s, instead of only one as in situation A. As the number of transmission links increase, also the delays created by the links increase. The increase of delays places more demands on the whole network, when the network has to fulfill strict delay requirements for constant delay services, such as speech. Further, since the number of transmission links in use increases, the load on the network increases.

SUMMARY OF THE INVENTION

An object of the invention is to optimize transmission links in a cellular telecommunications network, when a mobile station has moved from an area controlled by a first radio network controller to a second area controlled by a second radio network controller. Another object of the invention is to realize a method for reducing transmission delays between the controlling radio network controller and the base stations in a situation, when a mobile station has moved from an area controlled by a first radio network controller to a second area controlled by a second radio network controller. A further object of the invention is to realize a method for reducing network load in a situation, when a mobile station has moved from an area controlled by a first radio network controller to a second area controlled by a second radio network controller. A still further object of the invention is to alleviate the aforementioned problems.

The objects are reached by relocating the connection controlling entities from the first radio network controller to the second radio network controller, whereby the second radio network controller becomes the controlling radio network controller, and by optimising the links between the mobile switching center being used and the second radio network controller.

The invention describes the realisation of transmission link optimisation in a situation, where a mobile station has moved from a network area controlled by a first radio network controller (RNC) RNC1 to a network area controlled by a second radio network controller RNC2. Signalling associated with the procedure is executed between the two RNCs and a mobile switching center (MSC). The mobile station does not need to participate in the signaling, since the used radio resources remain the same. The object of this procedure is to optimise the utilisation of transmission links in the radio access network (RAN) being used and to minimise the transmission delay between the controlling RNC and the radio interface. This is realised by relocating the entities which control connections of a mobile station from the first RNC to the second RNC, and optimizing the transmission links between the MSC and the second RNC. Such controlling entities may comprises, e.g., the macrodiversity combining function, radio resource control block and associated user plane entities.

BRIEF DESCRIPTION OF THE DRAWINGS

The invention is described in more detail in the following with reference to the accompanying drawings, of which

DETAILED DESCRIPTION

Figure 1:
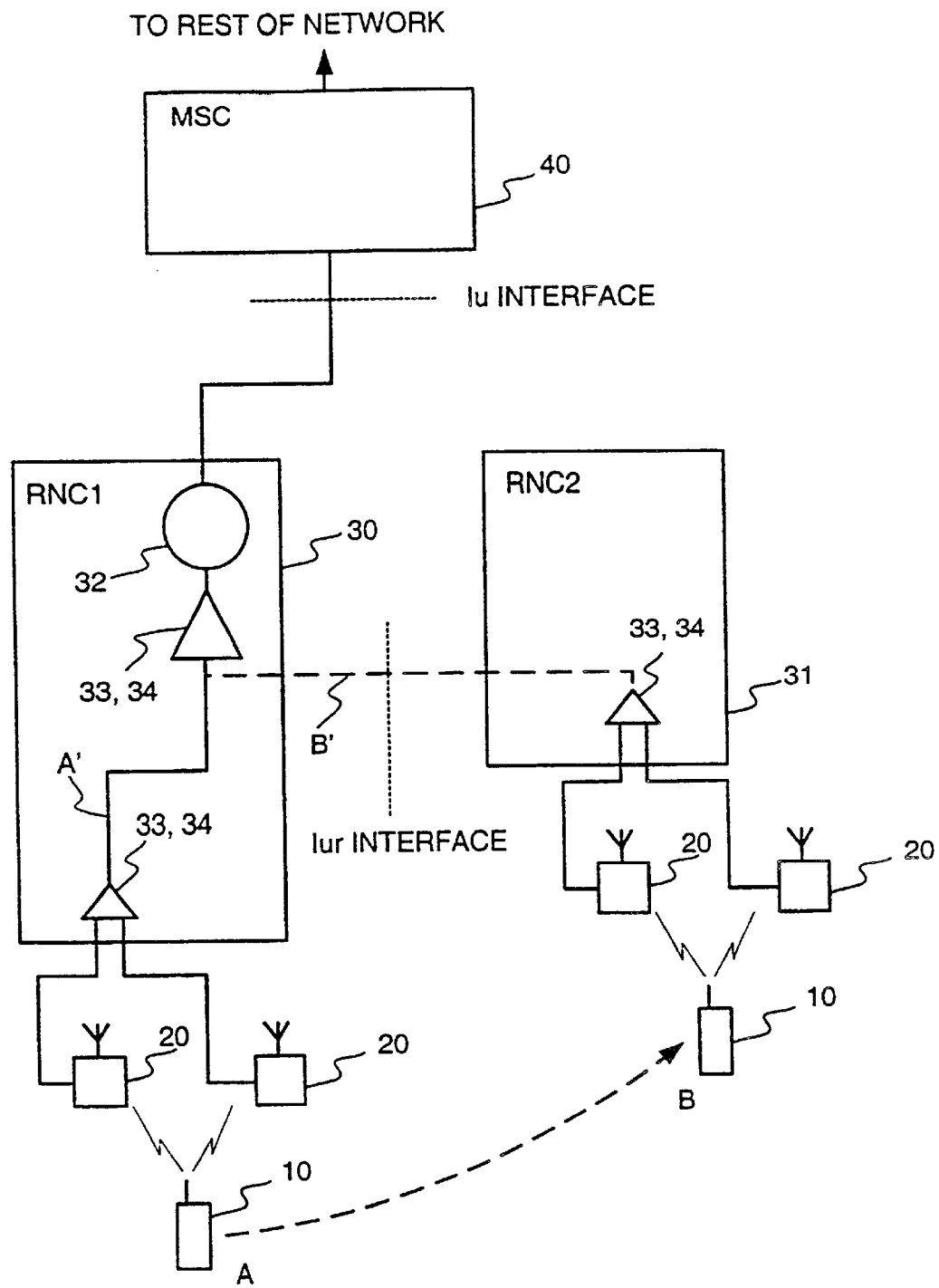
FIG. 1 illustrates a situation, which may occur in a prior art system after a hard handover.
Figure 2:
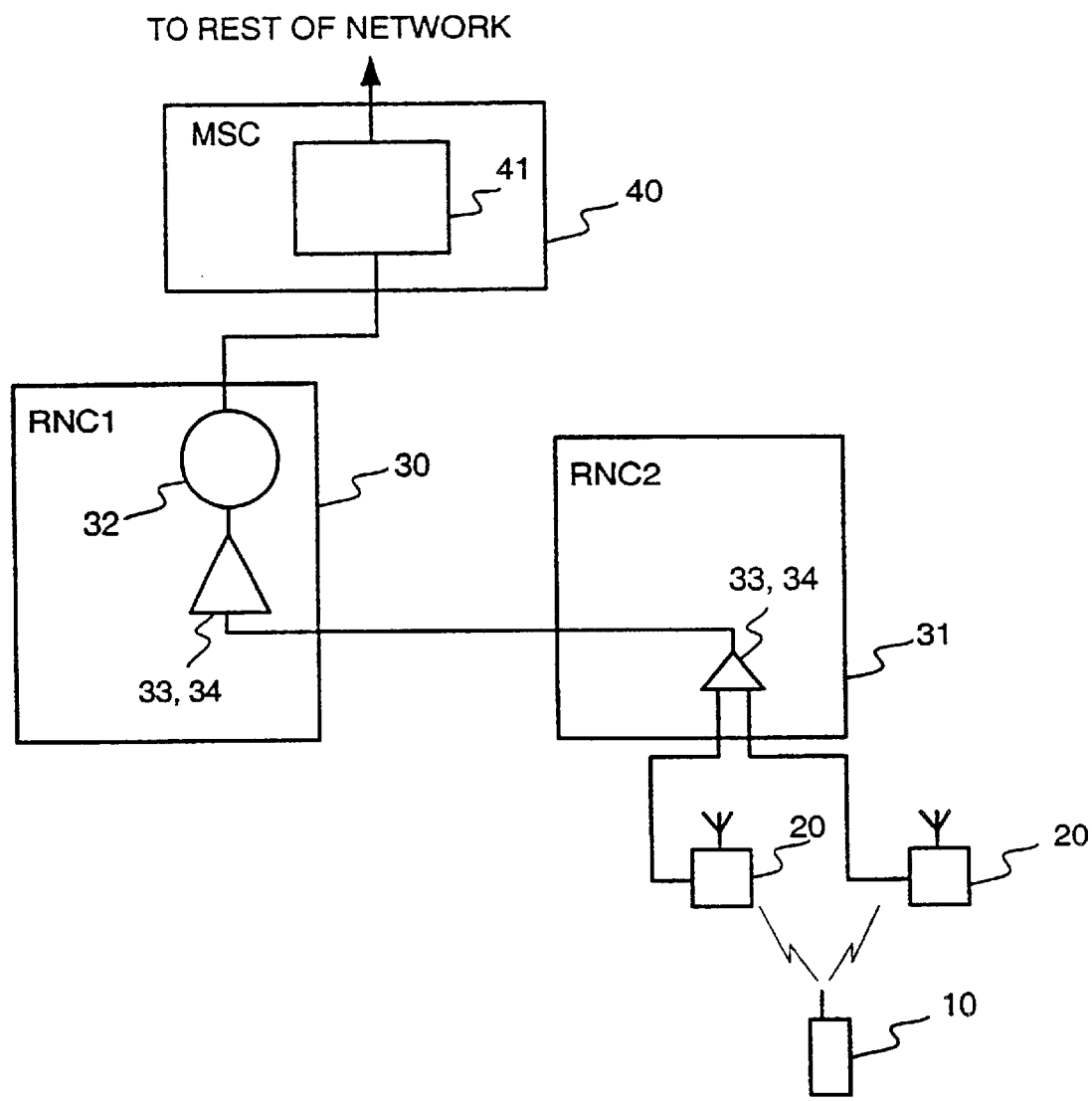
FIG. 2 illustrates a starting situation for the explanation of a method according to an advantageous embodiment of the invention.
Figure 3:
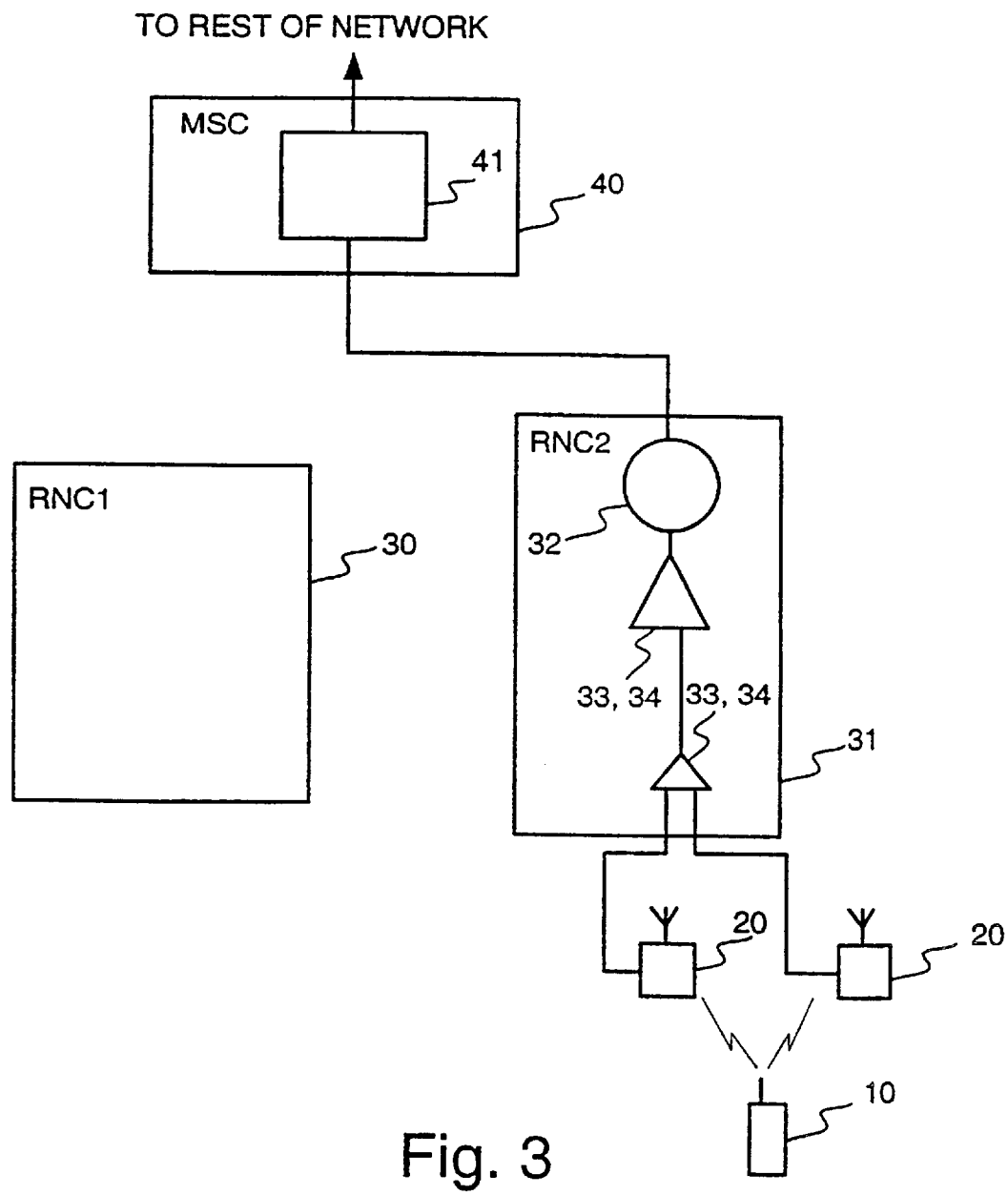
FIG. 3 illustrates the final situation after performing of a method according to an advantageous embodiment of the invention.
Figure 4:
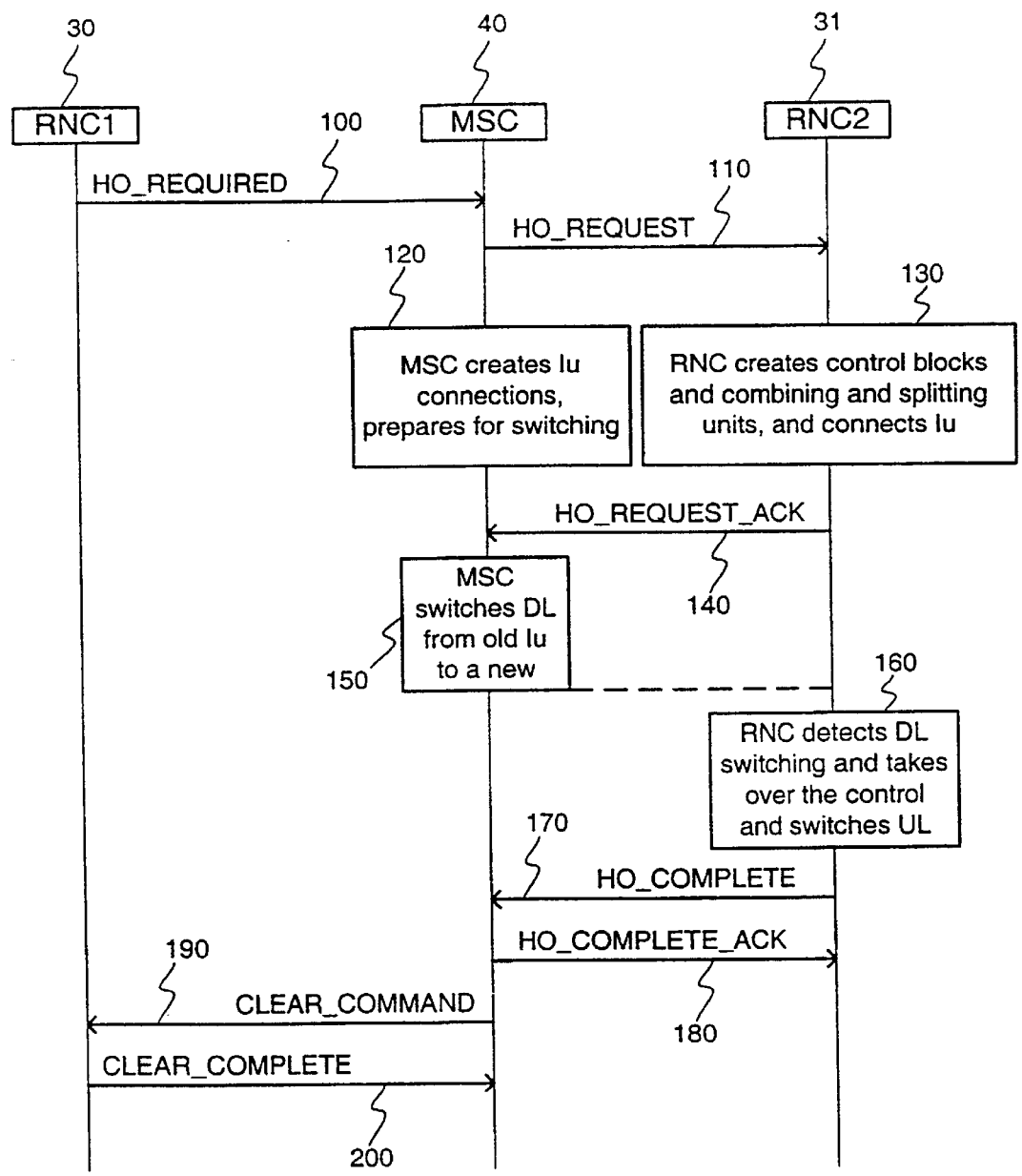
FIG. 4 illustrates the signalling according to an advantageous embodiment of the invention.

An advantageous embodiment of the invention is described in the following with reference to FIGS. 2, 3, and 4. FIG. 2 shows an initial situation, where a mobile station 10 (MS) has connections to base stations 20, which are controlled by another RNC 31 than the RNC 30 which controls the connections to the mobile station. In this starting situation, RNC1 30 controls the connection to the mobile station, while the connections are routed via RNC2 31, which controls the base stations in whose area the mobile station is currently located. This situation may arise, for example, when the mobile station initiates connections while located within a cell controlled by RNC1 30, and later moves away from that cell to another, which is controlled by RNC2 31. A mobile switching center 40 (MSC) forwards the connections from the rest of the network (not shown in FIG. 2) to the RNCs. The RNCs further comprise combining and splitting units 33, 34. Combining units 33 combine uplink signals belonging to the same bearer coming from different base stations, and splitting units replicate downlink signals to more than one base station. The MSC comprises, among others, a switching block 41. FIG. 3 illustrates the system of FIG. 2 after a handover. The signaling associated with a handover according to an advantageous embodiment of the invention is illustrated in FIG. 4.

The RNC which controls, i.e., manages, the connection to the MS, communicates with the MS using certain protocols, such as the RLC (Radio Link Control), MAC (Medium Access Control) and RRC (Radio Resource Control) protocols The RNC comprises certain functional blocks 32 for performing these protocols. These functional blocks are in the following called protocol control blocks 32. The protocol control blocks follow the protocol rules set by the network specifications, and include a memory for storing information associated with the current state of each protocol and other related information. These protocol control blocks are usually realised as computer programs, which take care of the procedures associated with each protocol.

In the starting situation, the mobile station has obtained radio resources from RNC2, since it is RNC2 that controls the base stations (BSs) which the MS is currently using. The connections at the interface between RNC1 and RNC2, i.e., the Iur interface, were set up by RNC1 when the mobile station moved from a cell controlled by RNC1 to a cell controlled by RNC2. These connections are identified by leg identifiers. The base station to RNC links are setup by the RNC controlling the base station in question, in this case, RNC2.

In practice, the MS may also be using radio resources from other RNCs. For simplicity, the initial situation shown in FIG. 2 only includes connections from base stations controlled by RNC2. In one embodiment of the invention, radio resources from other RNCs are released before performing a RNC handover described in the following. However, the invention is not limited to that embodiment. In other embodiments of the invention, radio resources from other RNCs may also be left unchanged during a RNC handover.

The handover procedure is initiated by a HO_REQUIRED message, which RNC1 30 sends 100 to the MSC 40. The message comprises information necessary for setting up the handover, namely identification of target RNC, leg identifiers for the Iur interface connections between RNC1 and RNC2, and protocol control block information specifying the protocols and the current state of the protocols in use.

Preferably, after sending of the HO_REQUIRED message, RNC1 is not allowed to change those characteristics of the connection or connections, which characteristics were specified in the HO_REQUIRED message. Otherwise, more signaling is needed between RNC1 and RNC2 before RNC2 takes over the connection in order to ensure that RNC2 has correct information about the state of the connections.

Upon reception of the HO_REQUIRED message the MSC starts to create new Iu connections to the target RNC. The MSC also sends 110 a HO_REQUEST message to RNC2, which message includes the same information necessary for setting up the handover.

Normal Iu connection setup procedures can be used to create the new Iu connections to the target RNC. The setting up of the Iu connections can be performed before, roughly at the same time, or after sending of the HO_REQUEST message to RNC2, depending on the chosen Iu connection setup procedure. MSC also prepares itself, i.e. the switching block of the MSC, to be able to switch each old Iu connection to its newly established counterpart, without any loss of data. FIG. 4 corresponds to such an embodiment of the invention, where the setting up 120 of Iu connections is performed after the sending of the HO_REQUEST message to RNC2.

The MSC is not the only entity suitable for creating the Iu connections between MSC and the target RNC. In another exemplary embodiment of the invention, the RNC2 performs the setting up of the new Iu connections between the RNC2 and the MSC, after receiving the HO_REQUEST message from the MSC.

MSC adds further information to the information received in the HO_REQUIRED message and passed on to RNC2 in the HO_REQUEST message, namely, at least a handover identifier. In such an embodiment of the invention, where the MSC takes care of creating the new Iu interface links between the MSC and the target RNC, the MSC also adds identifiers of the new Iu links to the information passed on to the target RNC in order to enable the target RNC to use the established Iu links in the particular handover.

The target RNC, RNC2, uses the Iur leg identifiers specified in the HO_REQUEST message to identify which of the currently active Iur interface legs are to be included in the handover procedure. The target RNC2 creates 130 protocol control blocks for the connections to the mobile station, and sets their state according to the protocol control block information contained in the message. Thereafter the protocol control blocks are able to take over controlling the MS after execution of the handover, and are set to wait for a trigger for starting the operation.

The HO_REQUIRED and HO_REQUEST messages also preferably comprise information about which identifier was used by RNC1 to identify itself to the active base stations. This information is needed after RNC2 takes over the connections to allow RNC2 to identify itself to the base stations and to allow the base stations to accept data from RNC2 and ignore data from RNC1.

The HO_REQUIRED message sent by the RNC1 may, in some embodiments of the invention, comprise a time reference proposal for the execution time of the handover. However, other ways of specifying the execution time are, specified later in this specification.

RNC2 creates 130 a combining unit for each of the uplink bearers and a splitting unit for each of the downlink bearers, whereafter RNC2 connects the new Iu links to corresponding splitting and combining units. A combining unit is a unit which combines the signals belonging to a single bearer from the base stations, which have received the same bearer. A splitting unit is a unit which distributes a bearer to multiple base stations for transmission.

RNC2 also prepares itself to switch the data stream coming from uplink combining units connected to the current Iur links identified by the leg identifiers in the HO_REQUEST message, to the new uplink combining units connected to the new Iu links. However, RNC2 can also prepare itself in other ways to switch the data stream. For example, in an another advantageous embodiment of the invention, RNC2 duplicates the uplink data stream and directs the duplicate to a newly created combining unit connected to the newly created Iu link, instructing the combining unit not to output any data yet. After such preparations, RNC2 can start sending data via the new Iu link simply by allowing the combining unit to output data.

The HO_REQUEST message sent by the MSC may also in some embodiments of the invention comprise a time reference proposal for the execution time of the handover. However, other ways of specifying the execution time are specified later in this specification.

The RNC2 needs information about the timing of the base stations in order to be able to adjust the sending time of downlink data units correctly, so that the data units are received by the base stations at the correct time for inclusion in the desired CDMA radio frames. The new protocol control blocks of RNC2 receive timing information determined by RNC1 as a part of the protocol control block information of the HO_REQUEST message. Since the transmission delays to the base stations are different at RNC2, the timing information needs to be checked. The timing information typically comprises information on the frame timing at each base station and transmission delays from the RNC to the base stations. Current cellular network systems and the UMTS specifications, for example, specify various methods for obtaining information about base station timing and transmission delays, any of which methods can be used in an embodiment of the invention. Therefore, these methods are not described here in further detail. RNC1 preferably includes in the timing information of the HO_REQUEST message also information about the length and the starting frames of the interleaving periods of the involved bearers, i.e. information concerning the services provided by the network for the mobile station. This service information does not need to be checked by the RNC2.

In such a situation, where the mobile station has active connections through more than one RNC, the target RNC, i.e. RNC2 in the present example, also creates new Iur links to and from the other RNC:s.

At the following stage, RNC2 signals MSC that preparations for the handover are completed by sending 140 a HO_REQUEST_ACK message to the MSC. This message comprises the identifier of the handover, for which RNC2 has prepared itself. The HO_REQUEST_ACK message sent by the RNC2 may also in some embodiments of the invention comprise a time reference proposal for the execution time of the handover. However, other ways of specifying the execution time are specified later in this specification.

After receiving the HO_REQUEST_ACK message from RNC2, the MSC prepares 150 itself for switching from the old Iu connections to RNC1 to the new Iu connections to the RNC2.

First, the switching of uplink connections in the MSC is discussed. In one embodiment of the invention, the MSC commands the switching element of the MSC to perform the switching immediately, when any activity at the new Iu uplink connection is detected. In another advantageous embodiment of the invention, the MSC sets up a multipoint-to-point connection connecting the Iu links participating in the handover from RNC1 and RNC2 to the MSC. In the multiparty connection embodiment, data coming from either of the RNC:s is forwarded by the MSC towards the intended destination. In one exemplary embodiment, the MSC sets up the multiparty connection by creating a combining means, which receives the uplink data from both RNC1 and RNC2, and outputs data, whenever any data is received in either of the inputs. Such a combining means may be created by setting up the switching elements of the switching unit of the MSC to perform such functions. In another advantageous embodiment of the invention, the combining unit also performs selection of data, which in case of same data arriving from both inputs, selects which of the two data streams is copied to output of the combining means. The combining means therefore removes duplicates if the same data is received from both inputs. The combining unit may perform this selection by checking, whether either of received units of data is incorrect, and by selecting the correct unit of data.

Next, the downlink arrangements at the MSC are discussed. The MSC starts to send data to the RNC2. In an advantageous embodiment of the invention, MSC duplicates the downlink data and sends them both through the old Iu links to RNC1 and through the new Iu links to RNC2. In this embodiment using data duplication, information indicating that the data is duplicated is preferably added to the downlink data units. This information identifying duplicated data simplifies the data processing at the base stations, if the base stations receive the same data both from RNC1 and RNC2.

In another embodiment of the invention, the MSC simply switches the downlink data transmission from RNC1 Iu links to RNC2 Iu links. This embodiment corresponds to the description of stage 150 in FIG. 4.

In an advantageous embodiment of the invention, the handover execution time is determined as follows. When RNC2 detects 160 that downlink data is coining from the MSC, it takes over controlling of the connections to the mobile station, and starts to send uplink data coming from the mobile station directly to the MSC through the new Iu uplink links. The switching block of RNC2 switches all uplink data to the new uplink combining unit, and ceases to forward the uplink data to the old Iur links towards RNC1. Similarly, the RNC2 ceases to forward downlink data coming from the RNC1 towards the base stations. This embodiment corresponds to the description of stage 160 in FIG. 4.

In another advantageous embodiment of the invention, the exact time of handover execution is found as follows. When the first data unit arrives through the new Iu links to the RNC2, the protocol control blocks examine the timing information described previously, and determine in which CDMA frame the data unit will be transmitted. The protocol control blocks perform this examining and determining for all bearers, and the first data unit to be sent towards the base stations determines the actual handover execution time.

The handover execution time can also be determined based on bearer interleaving periods. This procedure is explained later in this specification.

In some embodiments of the invention, the RNC handover execution time may be determined by a mobile station during a hard handover procedure, i.e. when a mobile station changes the base station it is using. The RNC handover procedure in conjunction with a hard handover procedure is explained later in this specification.

The data units are sent to base stations by the protocol control blocks through one or more splitting units, which replicate the data units to all base stations. The protocol control blocks also create any necessary header information, such as rate information or Frame Control Headers (FCH) needed for the CDMA frames.

In an advantageous embodiment, of the invention, all information created by the protocol control blocks in the RNC2 are marked with a RNC identifier identifying RNC2 as the creator of the information, in order to allow base stations to determine, that the information is generated after the handover execution. The identifier can be included, for example, to CDMA frame labels attached to each data and header unit. The identifier is advantageously selected by the new RNC. To avoid the same identifier to be selected, the old serving RNC, i.e. RNC1, indicates its identifier to the new serving RNC during the handover signalling, for example in the HO_REQUIRED message as described previously. However, the RNC identifiers can in some embodiments of the invention be specified by the MSC or some other controlling entity. Consequently, when a base station receives data units or control information related to the same connection, targeted to the same CDMA frame or frames and having different serving RNC identifiers, the base station discards the data units and control information marked with the old serving RNC identifier.

In such a situation, where the mobile station has active connections through more than one RNC, the target RNC, i.e. RNC2 in the present example, also begins forwarding data to and from the newly created Iur links links to and from the other RNC:s.

After completing the previous steps, RNC2 sends 170 a HO_COMPLETE message to the MSC, which message acknowledges that RNC2 has successfully completed the handover. After receiving the HO_COMPLETE message, MSC releases old connections to and from RNC1, and instructs RNC1 to release the connections as well by sending 190 a CLEAR_COMMAND message. In some embodiments of the invention, RNC1 may reply by sending a CLEAR_COMPLETE message after releasing the connections and performing any necessary other cleanup procedures.

In some embodiments of the invention, the MSC may also send 180 an acknowledgment message HO_COMPLETE_ACK back to the RNC2.

The handover procedure explained in connection with FIGS. 2 and 3 is only one exemplary embodiment of the invention. The handover procedure can be realised with many other signalling sequences as well. For example, RNC1 does not necessarily need to route the HO_REQUIRED message via the MSC. In a further exemplary embodiment of the invention, RNC1 initiates the handover by sending a HO_REQUIRED message directly to RNC2, and sends a separate HO_REQUIRED_MSC message to the MSC to command the MSC to begin preparations for the handover. As an another example, in some embodiments of the invention, RNC1 may send the HO_REQUIRED message directly to RNC2, after which RNC2 sends a corresponding message to the MSC to inform the MSC of the need for a handover.

In this specification, certain names have been used for various commands sent between the various functional entities. One example of such a command name is HO_REQUIRED. The invention is not limited to any specific command names; the command names can be different in different embodiments of the invention. Also, the names of various functional entities, such as the MSC and the RNC, may be different in different cellular networks. The names used in this specification are used in a specific exemplary design for a third generation mobile cellular network, and are not intended to limit the invention in any way.

Organising of Interleaving Periods

Typically, a cellular network provides various services to the user. The data transmission requirements such as transmission rate, the allowed bit error rate or maximum delay of the services are often different from service to service. Different requirements result in different interleaving periods being used for different bearers. With an interleaving period of 1, one data unit is sent in every frame. With an interleaving period of 2, one half of a data unit is sent in one frame. Generally, an interleaving period comprises n frames or other basic time units, where n is an integer between 1 and a specified maximum limit. In the general case, 1/nth part of a data unit is sent in one frame. Quite often, more than one part from more than one data unit are sent in one frame in order not to decrease the data transmission rate too much. The length of the interleaving period of a connection is set during the setup of the connection, as well as the starting frame of the interleaving period.

In an advantageous embodiment of the invention, the timing of each bearer is set in such a way that the interleaving periods of as many bearers as possible start at the same frame as often as possible. Optimally, the timing is set in such a way, that the interleaving periods of all bearers start at the same frame from time to time, with as small a repetition period as possible. This kind of timing simplifies the RNC handover, since then the handover can be executed at the beginning of a frame at which the interleaving periods of the bearers start. Without such interleaving period setup, strict time synchronization is required between the transmission of the various bearers in order not to exceed the specified interleaving periods during a handover.

Preferably the starting points of interleaving periods are set in such a way, that the starting frame of the interleaving period can be deduced from a simple rule, minimizing required calculations. For example, the interleaving periods are advantageously set to start at a frame, where the global frame number modulo the length of the interleaving period is a predefined number, such as one, or preferably zero. The global frame number is a number, which identifies the transmission frames. The global frame numbering scheme is commonly used in cellular telecommunication systems.

In a further advantageous embodiment of the invention, the lengths of the interleaving periods are adjusted according to a rule in order to further simplify the process. Preferably, the lengths of the interleaving periods are set to be powers of two, for example 2, 4, 8, or 16 frames and so on. When the length is a power of two the calculation, if the global frame number modulo the length of the interleaving period is zero, becomes extremely simple.

In this specification and in the accompanied claims, the length of interleaving periods is specified as the number of transmission frames, such as CDMA frames.

While the RNC handover can advantageously be timed to be executed at such a frame, when interleaving periods start, the alignment of interleaving periods according to the invention can also be utilized in other ways as well. For example, the alignment of interleaving periods also simplifies a normal hard handover, even when a RNC handover is not necessary.

RNC Handover Driven by a Hard Handover Procedure

Figure 5:
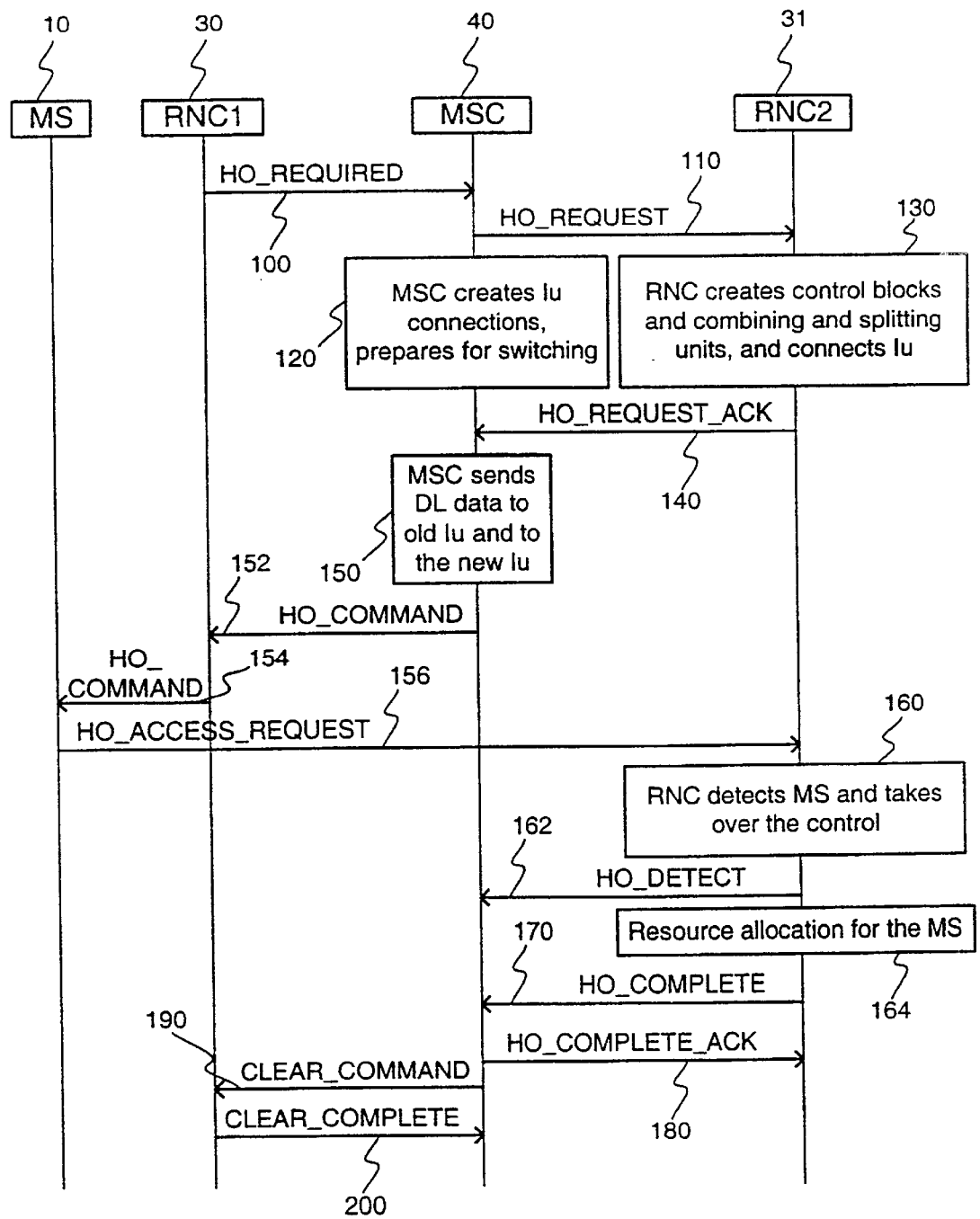
FIG. 5 illustrates the signalling according to an advantageous embodiment of the invention.

In an advantageous embodiment of the invention, the RNC handover is initiated by a so called hard handover, i.e., a handover of a mobile station from one base station to another, where the base stations are under the control of different RNCs. FIG. 5 illustrates one example of signaling used in an advantageous embodiment of the invention. This example corresponds to the situation when a mobile station moves from a cell controlled by RNC1 to a cell controlled by RNC2.

For clarity, most of the typical signalling between a mobile station and the network associated with a hard handover is not shown in FIG. 5. FIG. 5 presents only signalling associated directly with the RNC handover. Also, most of the signals and procedural steps shown in FIG. 5 were described in detail in connection with FIG. 4, and therefore a detailed description of these signals and procedural steps is not reproduced here.

First, RNC1 30 sends 100 a HO_REQUIRED message to MSC 40, which message preferably comprises the information described in connection with FIG. 4. The MSC sends a corresponding HO_REQUEST message to RNC2 31, and starts 120 the preparations for the handover. When RNC2 receives the HO_REQUEST message, RNC2 performs 130 the necessary preparations for handover. When RNC2 is ready for handover, it informs MSC by sending 140 an acknowledgement message HO_REQUEST_ACK to the MSC.

After receiving the acknowledgement, MSC starts to transmit downlink data via RNC2. Advantageously MSC sends the data both to RNC1 and RNC2, which corresponds to the example in FIG. 5. In other embodiments of the invention, MSC can switch the downlink data transmission from RNC1 to RNC2, thereby finishing downlink data transmission to RNC1.

Next, the MSC sends 152 a HO_COMMAND message to RNC1 indicating, that the handover may take place. RNC1 sends 154 a corresponding HO_COMMAND message to the mobile station. After receiving the HO_COMMAND message, the mobile station may trigger the handover at any time by sending 156 a HO_ACCESS_REQUEST message to RNC2.

In another advantageous embodiment of the invention, RNC2 creates the HO_COMMAND message, and includes the message in the HO_REQUEST_ACK-message it sends to MSC. Subsequently the MSC merely forwards the HO_COMMAND message to RNC1.

In a further advantageous embodiment of the invention, the HO_COMMAND message comprises information about the radio resources for use in the access request or in the activity after the access request. Such information may comprise, for example, channel information specifying the channel, on which the access request should be made. Such information may further comprise information about which channels have been received for the mobile station by the RNC2 for communication after the handover.

In the example of FIG. 5 the mobile station decides, when the handover is to be executed. However, the invention is not limited to this embodiment. For example, any of the known methods for triggering a hard handover may be used. Therefore, in other embodiments of the invention, RNC1 may act as the entity which decides the execution time for the hard handover and consequently the RNC handover. In other embodiments of the invention, RNC2 may act as that entity. For example, RNC1 and RNC2 may perform the preparations for the handover, after which RNC1 sends a message to RNC2, informing RNC2 that the RNC2 may execute the handover at any time. Since a hard handover can be executed also by the MSC, the MSC may as well decide the execution time in some embodiments of the invention.

When RNC2 receives the HO_ACCESS_REQUEST message, it performs the handover by taking over the control of the connections to the mobile station. In some embodiments of the invention, RNC2 may send 162 a HO_DETECT message to inform MSC, that RNC2 has detected the mobile station. Such a message is used in the GSM system. However, sending of the HO_DETECT message is not necessary in all embodiments of the invention, since the invention is not in any way limited to the GSM system.

After completing the previous steps, RNC2 sends 170 a HO_COMPLETE message to the MSC, which message acknowledges that RNC2 has successfully completed the handover. After receiving the HO_COMPLETE message, MSC releases old connections to and from RNC1, and instructs RNC1 to release the connections as well by sending 190 a CLEAR_COMMAND message. In some embodiments of the invention, RNC1 may reply by sending a CLEAR_COMPLETE message after releasing the connections and performing any necessary other cleanup procedures.

In some embodiments of the invention, the MSC may also send 180 an acknowledgment message HO_COMPLETE_ACK back to the RNC2.

Further Embodiments of the Invention

In some embodiments of the invention, more than one mobile switching center (MSC) are involved in the handover. This is the case when, for example, RNC1 is under control of a first MSC and RNC2 is under control of a second MSC. Another example of the involvement of more than one mobile switching center of corresponding entities is an inter-system handover. For example, when a mobile station moves from a cell of a first cellular system, say a GSM system, to a cell of a second cellular system, say a W-CDMA based system, the involved radio network controllers in each system are controlled by a MSC or a corresponding entity of the particular system. The various signaling sequences described previously in connection with FIGS. 4 and 5 can be used in such a situation as well, with the only change being that the RNCs send and receive messages to and from their respective controlling MSCs, not to and from the same MSC. The participating MSCs need to execute some signaling as well, for example, to execute an inter-MSC handover. However, since various inter-MSC handover methods are known by those skilled in the art, the signaling is not discussed here in detail. Inter-MSC handover is discussed, for example, in the PCT patent application WO 95/08898.

In some embodiments of the invention, a single RNC may have connections to and from more than one MSC. For example, the mobile station may have more than one connection, each of which come through a different MSC. Such a situation may arise for example in the UMTS system presently under development, when more than one call or connection is received from more than one core network through a single radio access network. In such an embodiment, the RNCs participating in the handover procedure preferably repeat the previously described signaling with each of the participating or corresponding core network entities.

The invention is not limited to identifying the source RNNC of data units by attaching RNC identifiers to the data units transmitted to base stations. In a further advantageous embodiment of the invention, a base station recognizes the RNC which transmitted a data unit from the transmission channel from which the data unit was received by the base station. For example, if the RNC2 sets up a new AAL2 layer connection to the base station, the connection setup signalling informs the base station, that the new correction comes from the RNC2. Afterwards the base station knows without explicit tagging of the data units that any data units received from the new AAL2 connection come from RNC2. The source RNC may also be identified by a certain AAL5 channel, a certain PCM communication link channel, or by any other specific channel. Similarly, the base station may know that data units from a certain second channel come from RNC1. Consequently, when the base station receives a data unit from the first radio network controller and a data unit from the second radio network controller, and said data units are directed to be sent in the same transmission frame, said base station discards said data unit received from the first radio network controller.

In a further advantageous embodiment, these source RNC identification methods may be used in combination. For example, the RNC1 can be identified by RNC identifiers attached to data units, and RNC2 by the communication channel transmitting the data units to the base station.

Although in the previous examples the mobile station is in connection with more than one base station simultaneously, the invention is not limited only to systems, in which a mobile station can have connections to multiple base stations. The method according to the invention can be used in any cellular telecommunication system using routing of connections via a controlling and a drift radio network controller or a corresponding entity.

The name of a given functional entity, such as the radio network controller, is often different in the context of different cellular telecommunication systems. For example, in the GSM system the functional entity corresponding to a RNC is the base station controller (BSC). Therefore, the term radio network controller in the claims is intended to cover all corresponding functional entities regardless of the term used for the entity in the particular cellular telecommunication system.

In view of the foregoing description it will be evident to a person skilled in the art that various modifications may be made within the scope of the invention. While a preferred embodiment of the invention has been described in detail, it should be apparent that many modifications and variations thereto are possible, all of which fall within the true spirit and scope of the invention.

What is claimed is:

1. A method for routing the control of at least one connection to a mobile station from a first radio network controller presently controlling the at least one connection to a second radio network controller controlling a base station within whose area the mobile station is currently located in a cellular telecommunication system, comprising the steps of:

transmitting state information of at least one protocol control block controlling at least one communications protocol, which protocol governs the communication of data between the mobile station and the first radio network controller on the at least one connection, from the first radio network controller to the second radio network controller;

initializing at least one protocol control block in the second radio network controller based on the state information received from the first radio network controller; and relocating control of said at least one communication protocol from said first radio network controller to said second radio network controller at a certain instant.

2. The method of claim 1, further comprising the steps of:

attaching, by said first radio network controller, a RNC identifier to downlink data units for informing base stations receiving said data units of the source of said data units; and attaching, by said second radio network controller, a RNC identifier to downlink data units for informing base stations receiving said data units of the source of said data units.

3. The method of claim 2, wherein if a base station receives a data unit identified by the identifier of said first radio network controller and a data unit identified by the identifier of said second radio network controller, and said data units are directed to be sent in the same transmission frame, said base station discards the data unit identified by the identifier of said first radio network controller.

4. The method of claim 1, further comprising the steps of:

receiving, by a base station, a data unit from one of said first and second radio network controllers via a communication link; and identifying, by said base station, which of said first or second radio network controllers transmitted said data unit based on which communication channel said data unit was received.

5. The method of claim 4, wherein if a base station receives a data unit from said first radio network controller and a data unit from said second radio network controller, and said data units are directed to be sent in the same transmission frame, said base station discards said data unit received from said first radio network controller.

6. The method of claim 1, wherein said second radio network controller determines the handover execution time.

7. The method of claim 1, wherein the mobile station determines the handover execution time.

8. The method of claim 1, wherein the handover is executed at the beginning of a transmission frame, at which the interleaving periods of at least two bearers start.

9. The method of claim 1, wherein:

the radio resources used by the mobile station are maintained the same during the relocation procedure.

10. The method of claim 1, wherein:

said steps are performed as a response to initiation of a radio interface handover of the mobile station.

11. The method of claim 1, further comprising, before the step of transmitting state information, the step of:

releasing any radio resources controlled by radio network controllers other than the second radio network controller.

12. The method of claim 1, further comprising the step of:

creating, by said second radio network controller, new Iur links to and from more than one radio network controller, where the mobile station has active connection through said more than one radio network controller.

13. The method of claim 1, wherein:

after initiation of the relocation, the first radio network controller is not allowed to change characteristics of the at least one connection whose control is to be relocated.

14. The method of claim 1, wherein:

said at least one protocol control block comprises at least a radio resource control block.

15. The method of claim 1, wherein:

said at least one protocol control block comprises at least a radio resource control block and a macrodiversity combining function.

16. The method of claim 1, further comprising the step of:

duplicating downlink data by a core network element for transmission to both the first radio network controller and the second radio network controller.

17. The method of claim 1, wherein:

the first radio network controller is a part of a first cellular system;

the second radio network controller is a part of a second cellular system; and said first and second cellular systems are different cellular systems.

18. The method of claim 1, wherein:

one of the first and the second radio network controllers is a base station controller of a GSM network and the other is a radio network controller of a W-CDMA system.

19. The method of claim 1, wherein:

the first and the second radio network controllers are radio network controllers of a W-CDMA system.

20. The method of claim 1, further comprising the step of:

repeating, when the mobile station has a plurality of connections coming through a plurality of core network elements, said transmitting and initializing steps for connections of each of said plurality of core network elements.

21. The method of claim 1, further comprising the step of:

sending an identifier associated with the relocation as a parameter of a message to a core network element participating in the relocation.

22. The method of claim 1, further comprising at least one of the steps of:

transmitting said state information from said first radio network controller to a core network element in a first message;

transmitting said state information from said core network element to said second radio network controller in a second message;

creating Iu interface connections from said core network element to said second radio network controller;

creating a protocol control block in said second radio network controller;

sending an acknowledgement message from said second radio network controller to said core network element;

receiving an access request message from a mobile station by said second radio network controller; and taking over control of the at least one connection by said second radio network controller as a response to receiving said access request message.

23. A system for controlling connections to a mobile station in a cellular telecommunications network, comprising:

a first radio network controller presently controlling at least one connection to the mobile station;

a protocol control block in said first radio network controller for controlling at least one communication protocol which governs the communication of data on the at least one connection between the mobile station and the first radio network controller; and a second radio network controller which controls a base station within whose area the mobile station is currently located; wherein:

said first radio network controller is arranged to send information specifying the state of said protocol control block to said second radio network controller;

said second radio network controller is arranged to initialize at least one protocol control block in the second radio network controller based on the state information received from the first radio network controller; and said second radio network controller is arranged to take over control of said at least one connection at a certain instant.

24. A method for switching control of at least one connection with a mobile station from a first radio network controller (RNC) presently controlling the at least one connection to a second RNC controlling a base station in whose area the mobile station is currently located, comprising the steps of:

transmitting state information of said at least one mobile terminal connection from the first RNC to the second RNC, wherein a first protocol control block located in the first RNC controls the at least one mobile terminal connection according to at least one protocol, and wherein the transmitted state information comprises information specifying the at least one protocol and a state of said at least one mobile terminal connection according to the at least one protocol;

initializing a second protocol control block in the second RNC using the state information received from the first RNC; and relocating control of the at least one mobile terminal connection from the first RNC to the second RNC by switching control from the first protocol control block in the first RNC to the second protocol control block in the second RNC.

25. The method of claim 24, further comprising the steps of:

setting up a new Iu interface connection between a mobile switching center (MSC) and the second RNC, wherein the at least one mobile terminal connection is routed through said MSC and said new Iu interface connection relates to the at least one mobile terminal connection; and tearing down an old Iu interface connection between the MSC and the first RNC, wherein said old Iu interface connection related to the at least one mobile terminal connection.

* * * * *